United States Patent [19]
Liff et al.

[11] Patent Number: 5,713,485
[45] Date of Patent: Feb. 3, 1998

[54] DRUG DISPENSING SYSTEM

[75] Inventors: Harold J. Liff, Lexington; Brian T. Hart, Bedford; Robert L. Wallace, Pepperell, all of Mass.; Arthur A. Berube, Hampstead, N.H.

[73] Assignee: ADDS, Inc., North Billerica, Mass.

[21] Appl. No.: 544,623

[22] Filed: Oct. 18, 1995

[51] Int. Cl.⁶ ......................................................... G07F 11/00
[52] U.S. Cl. ........................... 221/2; 221/129; 364/479.07
[58] Field of Search ......................................... 221/2, 3, 123, 221/124, 122, 131, 7, 15; 364/479.01, 479.11, 479.07

[56] References Cited

U.S. PATENT DOCUMENTS

| | | | |
|---|---|---|---|
| 3,917,045 | 11/1975 | Williams et al. | 194/4 |
| 4,546,901 | 10/1985 | Buttarazzi | 221/10 |
| 4,655,026 | 4/1987 | Wigoda | 53/55 |
| 4,695,954 | 9/1987 | Rose et al. | 364/413 |
| 4,717,042 | 1/1988 | McLaughlin | 221/3 |
| 4,732,411 | 3/1988 | Siegel | 283/75 |
| 4,766,542 | 8/1988 | Pilarczyk | 364/413 |
| 4,785,969 | 11/1988 | McLaughlin | 221/2 |
| 4,818,850 | 4/1989 | Gombrich et al. | 235/494 |
| 4,837,719 | 6/1989 | McIntosh et al. | 364/569 |
| 4,847,764 | 7/1989 | Halvorson | 364/413.02 |
| 4,872,591 | 10/1989 | Konopka | 221/129 |
| 4,911,327 | 3/1990 | Shepherd et al. | 221/3 |
| 4,918,604 | 4/1990 | Baum | 364/413.01 |
| 4,967,928 | 11/1990 | Carter | 221/2 |
| 4,980,292 | 12/1990 | Elbert et al. | 435/289 |
| 4,991,740 | 2/1991 | Levasseur | 221/129 |
| 5,014,875 | 5/1991 | McLaughlin et al. | 221/2 |
| 5,047,948 | 9/1991 | Turner | 364/479 |
| 5,292,029 | 3/1994 | Pearson | 221/2 |

(List continued on next page.)

FOREIGN PATENT DOCUMENTS

95/25423  9/1995  WIPO.

OTHER PUBLICATIONS

RxOBot, "The Safe Solution for Medication Management", Automated Healthcare Inc., Pharmacy Robotics, 261 Kalfa Drive, 1994, 15238–2873 (Publication).
Meditrol, Automation Systems, "Fact Sheet", 9800 Center Parkway, Suite 600, Houston, TX 77036 (Publication).
OMNICELL™, "OMNICELL See & Touch™ Supply System", OMNICELL Technologies, Inc., 1101 East Meadow Drive, Palo Alto, CA 94303 (1994) (Brochure).
$R_xOBOT$™, "The Safe Solution for Medication Management", Automated Healthcare, Inc., Pharmacy Robotics, 261 Kappa Drive, Pittsburgh, PA 15238–2873 (Brochure).
Meditrol™ Automation Systems, "Fact Sheet", Meditrol Automation Systems, 9800 Centre Parkway, Suite 600, Houston, TX 77036 (Brochure).
Vangard Labs, Inc., "Reverse Number 4x25 for Controlled Substances", VanGard Labs, Inc., 890 L. Rogers Wells Blvd., Glasgow, KY 42141 (Apr. 1993) (Brochure).
Baxter, "Elevate Your Capacity to Perform—Begin With Productivity Systems," Baxter Healthcare Corporation, I.V. Systems Division, Productivity Systems, Route 120 & Wilson Road, Round Lake, IL 60073 (Dec. 1993) (Brochure).

*Primary Examiner*—Kenneth Noland
*Attorney, Agent, or Firm*—Hamilton, Brook, Smith & Reynolds, P.C.

[57] ABSTRACT

An automated drug dispensing system includes a cabinet adapted to store a variety of prepackaged pharmaceuticals in a plurality of bins for filling patient prescriptions. Each bin stores a particular variety of packaged multiple-dose pharmaceutical. Each variety of pharmaceutical is associated with a particular code. A controller receives request signals and in response generates dispense signals. Each bin includes a dispenser coupled to the controller for dispensing the packaged pharmaceuticals therefrom in response to a dispense signal sent from the controller. After a package is dispensed, a code reader determines the code of the dispensed package and verifies whether the code on the dispensed package matches the code of the requested package.

32 Claims, 12 Drawing Sheets

U.S. PATENT DOCUMENTS

| | | | |
|---|---|---|---|
| 5,314,243 | 5/1994 | McDonald et al. | 312/215 |
| 5,337,919 | 8/1994 | Spaulding et al. | 221/2 |
| 5,348,061 | 9/1994 | Riley et al. | 141/104 |
| 5,390,796 | 2/1995 | Kerfoot, Jr. | 206/534 |
| 5,401,059 | 3/1995 | Ferrario | 221/2 |
| 5,404,384 | 4/1995 | Colburn et al. | 377/6 |
| 5,431,299 | 7/1995 | Brewer et al. | 221/2 |
| 5,495,961 | 3/1996 | Maestic | 221/3 |

DRUG DISPENSING SYSTEM

BACKGROUND OF THE INVENTION

Automated pharmaceutical delivery systems have been in use for over thirty years. The initial purpose of such systems was to reduce the high rates of medication errors associated with manual distribution. In modern times, automated systems present more sophisticated advantages. These include: further reduction of errors, lower costs associated with pharmaceutical distribution, reduction of personnel, inventory control, substance control, automated documentation, and relieving professional pharmacists of many tasks.

The current state of the art of automated pharmaceutical delivery systems, otherwise known as medication management devices generally fall under three categories: automated devices in the central pharmacy area; automated devices in the patient care unit; and point-of-care information systems.

The primary goal of centrally-located devices is to replace or improve the current manual process for filling unit dose carts. These devices offer the advantage of a single, centralized inventory and a lower overall inventory. Disadvantages of such devices include their large size, high cost, and reliance on efficient delivery systems.

Patient care unit-based devices replace the traditional manual unit dose cart filling and delivery system and provide increased control over floor stock. Advantages of such systems include their smaller size and lower cost relative to centrally-located devices, immediate access to medications, and automated documentation of medication administration. Disadvantages include application to unit dose levels only, increased costs due to the maintenance of multiple inventories in multiple units, additional time required to restock multiple devices, and larger inventory.

Point-of-care systems are designed to enable immediate exchange of patient data at the bedside. Such systems allow for rapid access to patient information, fast documentation, integration of hospital information systems, and immediate verification of drug administration. Primary disadvantages of point-of-care systems include high cost associated with placing hardware in each room, networking the system, and security issues associated with personal data access.

The above-described systems offer solutions for medication management in large hospitals where the large expense associated with large centrally-located pharmacy systems, decentralized patient care units, and point-of-care systems at the bedside are justifiable for unit-dose dispensing and verification. These systems fail to address efficient and economical medication management at medium size facilities, for example health maintenance organizations which cannot justify the expenses associated with the large and costly aforementioned systems. Furthermore, while the above systems provide a solution for unit-dose dispensing for individual patients, they fail to address the issue of filling weekly or monthly prescriptions in a cost-effective manner.

SUMMARY OF THE INVENTION

The present invention combines computer hardware and software, a telecommunications capability, and a medication container dispensing cabinet to form a complete in-office dispensing system. This enables drug prescription dispensing in volume by a physician, pharmacist, or other licensed practitioner directly to the patient at a clinic, group practice, or other location outside a pharmacy or hospital. The system provides a convenient, safe, automated, and low cost drug delivery system for the patient.

The present invention is directed to an apparatus and method for automated dispensing of packaged pharmaceuticals. The apparatus of the invention includes a cabinet housing for storing a variety of packaged pharmaceuticals in a plurality of bins. Each bin stores a particular variety of packaged pharmaceutical where each package typically contains a plurality of unit doses as normally provided in a pharmacy filled prescription. Each variety of pharmaceutical is associated with a particular code marked on the package. When the packages are loaded into the system, the loader scans each bar coded package with a bar code reader so that the data base for the unit properly reflects the packages contained in the unit. For dispensing a controller receives request signals and in response generates dispense signals. Each bin includes a dispenser coupled to the controller for dispensing a packaged pharmaceutical therefrom in response to a dispense signal sent from the controller. When the package is dispensed, a code reader determines the code of the dispensed package and verifies whether the code of the dispensed package matches the code of the requested package.

The dispensing process can be initiated by an authorized user at a computer terminal connected to the cabinet controller. Alternatively, a computer can be used to program a card or slip with patient information, with the cabinet being adapted for receiving the card, for automatic dispensing directly to the patient.

A plurality of the cabinet housings can be installed in a modular or daisy-chained configuration in which a single controller operates a plurality of housings. In a preferred embodiment of the apparatus of the invention, the bins are in the shape of vertically-disposed columns shaped to store a plurality of bottles stacked vertically. Each bottle is sealed and contains a selected number of doses prior to being dispensed. Pharmaceutical packages are laid on top of each other within each column and are fed by gravity from the top of the column and exit at the bottom of the column on a first-in-first-out basis. Each column includes a replaceable label containing a code which matches the code disposed on the packages placed in that column. Package coding is preferably accomplished by bar code which can include the drug identification number, dosage expiration date and number of tablets. The controller is preferably a computer. In an automated system, sensors mounted in the bins monitor the inventory of the packages in each bin and detect jammed bins.

The cabinet is preferably mounted on a wall or on a supporting cart as a stand alone unit. A ramp delivers a dispensed pharmaceutical to a drop point. The ramp is preferably sloped so that gravity delivers the dispensed pharmaceutical without the need for other conveying means. A label printer is coupled to the controller for printing a patient specific prescription label for attaching to a dispensed pharmaceutical package. The prescription label can include a printed picture of the pharmaceutical contained in the package. A document printer is likewise coupled thereto for printing instructions specific to the dispensed pharmaceutical for use by the patient or medical practitioner. In a preferred embodiment, the printers are inhibited until the bar-code reader verifies that proper dispensing of the pharmaceutical has occurred.

A preferred method of using the invention for a clinical trial includes dispensing a pharmaceutical and a placebo in different packages and monitoring use thereof. Clinical trials are commonly used in the evaluation of the safety and effectiveness of drug protocols in the pharmaceutical industry. These trials can typically take the form of distributing the drug being tested and a placebo to a selected patient population and then monitoring the outcome to determine the drug's effectiveness. The dispensing system of the present invention is particularly well suited to aid in the controlled distribution of both the drug (or drugs) under test and the placebo used in these clinical trials. Due to the accurate labelling, record keeping and remote distribution capabilities, and the ability to dedicate specific units to a particular trial the conduct of these trials can be done more safely and accurately.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE PREFERRED EMBODIMENTS

The present invention provides safe pharmaceutical prescription dispensing directly by physicians, pharmacists, and other licensed practitioners operating in small to medium size locations in a cost-effective manner. Prepackaged pharmaceuticals are stocked at nearby municipal service centers and distributed to the health care locations as needed. The inventory is continually and automatically monitored by a host computer at the location. Inventory is ordered on a just-in-time basis by the computer. In this manner, prepackaged multiple-dose pharmaceuticals are available to practitioners at the health-care facility for immediate filling of patient prescriptions.

The present invention offers significant advantages to physician group practices. The system improves customer service and enhances the image of the group practice. Drug theft is prevented by securing the pharmaceuticals in a closed system and inventory is kept low. The system meets state pharmacy, safety, and regulatory compliance laws, whereas many manual dispensing systems do not. A pharmaceutical distributor can handle all inventory planning, financing, maintenance, and ordering with minimal interaction with group practitioners. Disruptive telephone calls to the physician from pharmacists are minimized. Further, physicians can gain immediate access to a patient's pharmacy records currently unavailable to him.

Managed care providers, for example, Health Maintenance Organizations and Pharmacy Benefits Managers also realize significant advantages from the present invention. The invention increases the likelihood that a patient will receive the required treatment, because the pharmacy is available at the doctor's office. Labor costs for in-house pharmacies are reduced, allowing staff reductions or reassignments. In-house drug dispensing can be extended to physician-staffed satellite clinics and other locations not suitable economically for conventional pharmacies. The system enables automated patient compliance enhancing programs, drug utilization analysis, and the use of other emerging pharmacy management opportunities to reduce costs and improve patient compliance and wellness. Drug costs are reduced by formulary control, thereby encouraging generic substitution of name brand drugs. Inventory is tracked automatically by the drug distributor headquarters, thus preserving professional time for patient care.

The present invention also offers significant advantages to the patients. Drugs are provided immediately at the physician's office, avoiding an inconvenient trip to a pharmacy. This is particularly important to mobility-impaired patients and eliminates a major source of drug non-compliance. Electronic third-party payor cards can be used for drug purchases at the doctor's office. The patient can obtain prescription drugs at prices competitive with retail discounters. The physicians are able to track prescription compliance which can result in faster recovery.

Figure 1:
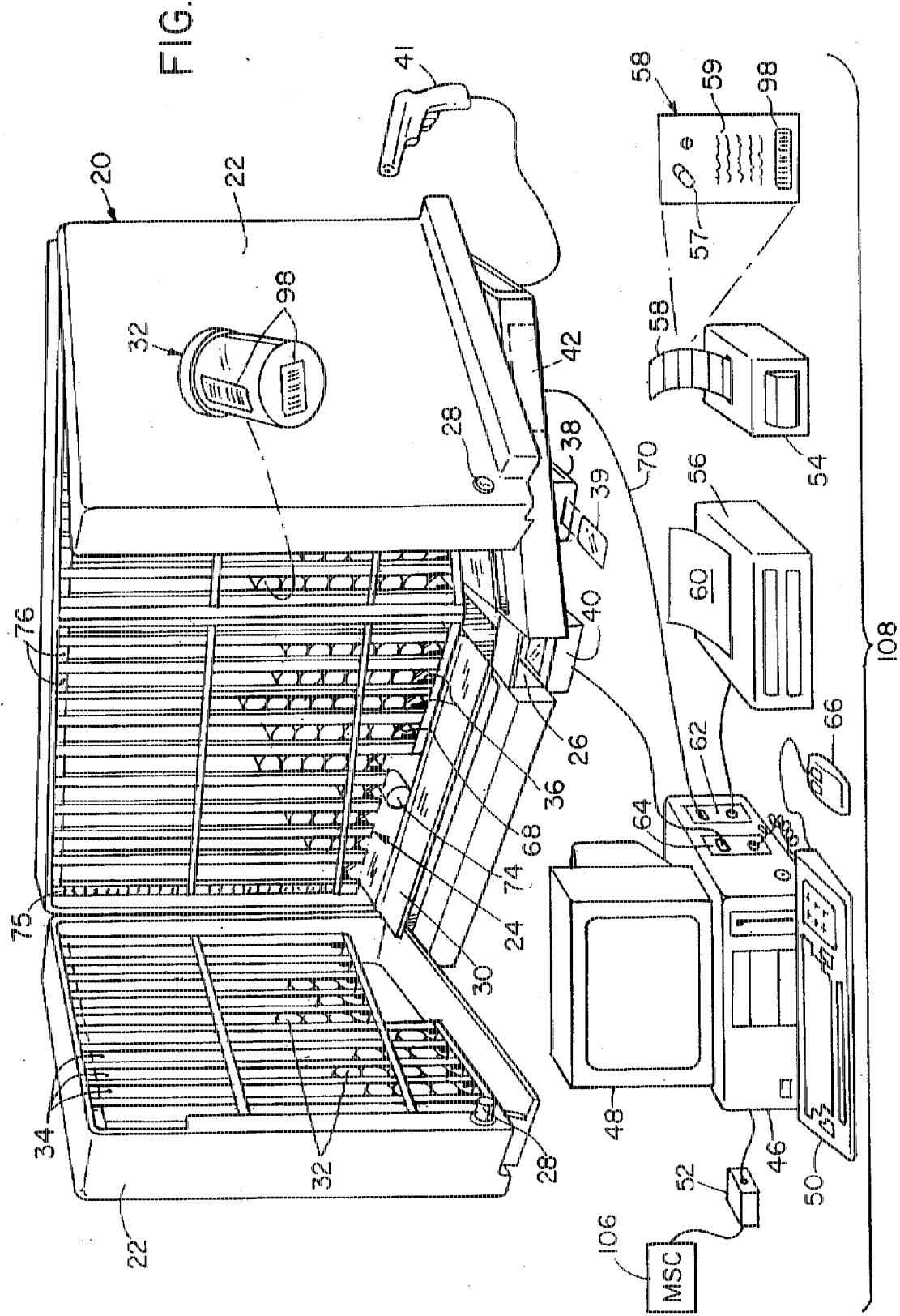
FIG. 1 is a diagram of preferred embodiment of an automated drug dispensing system in accordance with the present invention.

The apparatus of a preferred embodiment of the invention will now be described. FIG. 1 is a diagram of an automated drug dispensing system in accordance with the present invention. The primary components of the system include a remote control dispenser (RCD) cabinet 20, a host computer 46, a modem 52, a document printer 56, and a label printer 54. The cabinet 20 includes a rack 24 comprising a plurality of bins, preferably in the shape of columns 34. Packages 32 such as drug bottles, containing pharmaceuticals of various types are distributed among the columns 34, each column 34 containing a separate type of pharmaceutical. Four racks 24 are enclosed in the cabinet 20 chamber, two in the main cabinet 20 and two on the doors 22. The doors are secured by locks 28.

A licensed user, for example, a doctor, pharmacist, nurse, or other medical practitioner qualified to fill patient prescriptions, operates the system at the host computer 46, using a keyboard 50 and mouse 66 for input and receiving visual feedback at a monitor 48. Using the keyboard 50, a user enters a command to request dispensing of a particular packaged pharmaceutical variety 32 for a particular patient. The computer 46 transmits the request via an interface 70 to a controller 42 located on the RCD cabinet 20. The controller 42 interprets the command sent from the computer 46 and enables a dispensing actuator 68 in the appropriate column 34. The lowest package 32 in the appropriate column 34 is released from the column 34 and ejected onto a ramp 30. The released package 74 slides down the ramp 30 into an opening 26, where the released package 74 is made available to the dispensing party for transfer to the patient. A bar code reader 40, located near the dispensing opening 26, reads a code 98 on the dispensed package 74 and transmits the bar code information to the computer 46, which informs the user whether the code 98 on the dispensed package 74 matches that which was requested by the user. The bar code 98 can be disposed on the side, top, and/or bottom of the package 32. In an automated embodiment of the system, sensors 36 located on each column 34 monitor the dispensing process and notify the controller 42 of any package jams. The sensors 36 also monitor inventory of the columns 34 and notify the computer 46 through controller 42 that a particular column is empty or near empty.

Alternatively, the prescription can be dispensed directly to the patent. A card reader 38, mounted directly on or near the cabinet, is adapted to receive a card 39 from a patient. The card is programmed with patient information by a licensed practitioner. The patient inserts the card 39 in the card reader 38 and receives his medication automatically from the cabinet. The medication bottle 32 may be filled with a single dose of medication for a particular patient, or can include weekly or monthly doses. This embodiment is especially useful in large institutions, such as prisons, where many individuals require medication on a regular basis.

Upon validating the bar-code 98 of the dispensed package 74, the computer generates a label 58 containing prescription information at a label printer 54 to be placed on the package, and generates a document 60 at a document printer 56 containing additional instructions for the patient or practitioner. A modem 52 enables periodic or continuous communication between the host computer 46 and other computers in the network so that a complete inventory and status of each remote control dispenser cabinet is available at all times. Several remote control dispenser cabinets 20 can be integrated into a single installation operated by a single computer 46. The cabinets 20 can each be individually connected to the host computer 46, or may be daisy-chained, with only one cabinet 20 in the chain connected to the host 46.

Figure 3:
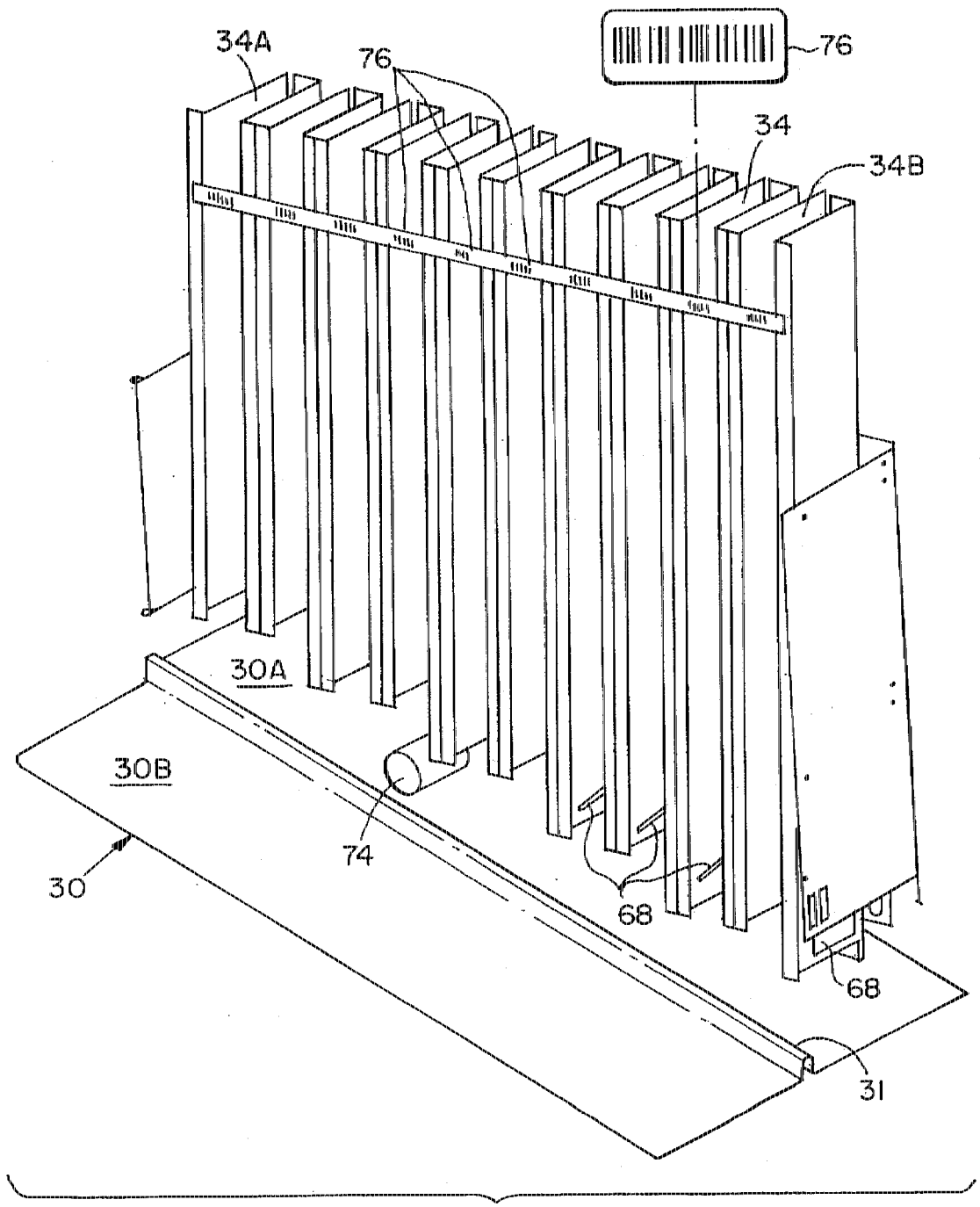
FIG. 3 is a block diagram of a preferred embodiment of a cabinet rack in accordance with the present invention.

A typical remote control dispenser cabinet 20 contains forty columns 34 for holding and dispensing the prepackaged pharmaceuticals. Each rack 24 includes ten columns 34, as shown in FIG. 3. Two racks are disposed on each side of the cabinet, one in the main cabinet area 20, and one on the door 22, such that when the door 22 is closed, the racks 24 face each other. A typical column will hold up to 13 packages of a given pharmaceutical. The columns at the ends of the cabinet 34A are shorter than the columns nearest the center of the cabinet 34B to accommodate the sloped ramp 30. The ramp 30 receives a dispensed pharmaceutical package, and directs it toward the dispensing area 26 in the center of the cabinet 20. A raised ramp divider 31 divides the ramp 30 into two sections 30A, 30B, each section for dispensing pharmaceutical packages from each rack. At the top of each column 34 is a replaceable bar code label 76 which identifies the pharmaceutical contained in that column and the appropriate column number. At the time of loading the cabinet, the column bar code label 76 is matched against the package label 98 to be loaded to verify that the correct pharmaceutical package 32 is placed in each column.

Referring back to FIG. 1, the RCD controller 42 receives commands from and transmits status information to the host computer 46 via the controller interface 70. A request command sent from the host computer 46 identifies the pharmaceutical package 32 to be dispensed. In response, the RCD controller 42 activates the appropriate dispenser 68, thereby releasing a single package of the variety requested. A parallel or serial I/O interface 62 at the host computer 46 provides a sufficient communication channel. The simplest interface is a unidirectional channel from the host computer 46 to the controller 42. A full duplex implementation allows the controller 42 to transfer status information back to the host 46. Status information may include errors such as package jams, empty columns, or other cabinet status. Availability of such information prevents inconsistencies in the database and provides the operator with recovery procedures. This would require adequate sensors 36 to be mounted in appropriate positions on the RCD cabinet 20.

The bar-code reader 40 can be mounted directly on the unit or can comprise a hand-held unit 41. It verifies proper loading of the RCD cabinet 20 and proper dispensing of each pharmaceutical package 32. Before a column 34 is loaded with packages 32, the column bar code label 76 is compared with the bar code label 98 of each package 32 inserted into the column 34. Each time a package 74 is dispensed from the cabinet 20, the package bar code label 98 is scanned by the bar code reader 40 to verify that the correct pharmaceutical has been dispensed. The bar code reader 40 is interfaced to the host computer 46 through a standard keyboard wedge 64. The wedge 64 makes the bar code reader 40 input via the bar code interface 72 appears to be coming from the keyboard 50. Such an interface is a simple and reliable interface to the pharmacy software operating on the computer 46. The bar code reader 40 must be highly reliable and provide a high first read rate. Label printing on the pharmaceutical packages 32 must be of high quality to accommodate this. During loading, the bottles are loaded into each column up to a certain height the highest bottle in the column is positioned adjacent a bar coded column label 75 running along each column. Thus, the number of bottles in each column can be recorded at loading and tracked during use.

The host computer 46 runs the pharmacy software, provides a user interface, and supports the RCD controller 42, bar code reader 40, and modem 52. A standard off-the-shelf personal computer and operating system are sufficient to meet these requirements. As described above, the keyboard 50 and mouse 66 receive input from the user and the monitor 48 provides visual feedback. The document printer 56 prints documentation 60 such as detailed instructions and a label printer 54 prints package labels 58, for example, prescription information 59 for adherence to the dispensed package 74. The prescription label 58 may also include a printed picture of the pharmaceutical 57 contained on the bottle to provide additional security.

The modem 52 provides a communication link between the municipal service center (MSC) 106 and the remote control dispenser 108. Through this link, inventory of each RCD cabinet 20 is automatically monitored and updated in the MSC 106 computer. The modem link also serves as a medium to issue restock orders, update pharmacy software running on the host computer 46, and provide remote diagnostics. The modem can be compatible with standard telephone lines and can be capable of transferring data at sufficient rates.

The pharmacy software operating on the host computer 46 is a standard commercial software package which provides standard administrative and accounting capabilities. The pharmacy software also supports the unique features of the remote control dispenser system. These include: data communication with the RCD controller 42 via parallel or serial I/O interface 62; data communication with the bar code reader 40 via keyboard wedge 64; data communication with the municipal service center via modem 52; printing of labels 58 with the label printer 54 and printing of documentation 60 with the document printer 56. The software is described in further detail below in conjunction with FIGS. 7A and 7B.

The cabinet 20 and rack 24 are preferably fabricated from aluminum, stainless steel, or plastic to be fully compatible with a clinical setting. The rack 34 can be modified to provide for a diversity of packages including various box and bottle sizes, unit-of-use packaging, liquids, syringes, and various non-prescription products, for example, medical supplies.

The computer 46 can comprise a portable terminal, a notebook computer, or a hand-held personal digital assistant. Voice recognition or voice prompted software can be employed using a telephone or wireless local area network. Voice recognition systems can use a generic or a user-customized system and can include voice signatures. The objective is to maximize system flexibility and ease of use for the doctor and staff without compromising safety. The remote control dispenser system can be utilized as a free-standing system, as a local network integrated with physician office computers, or as a centralized network in conjunction with product release at a remote location.

Figure 4:
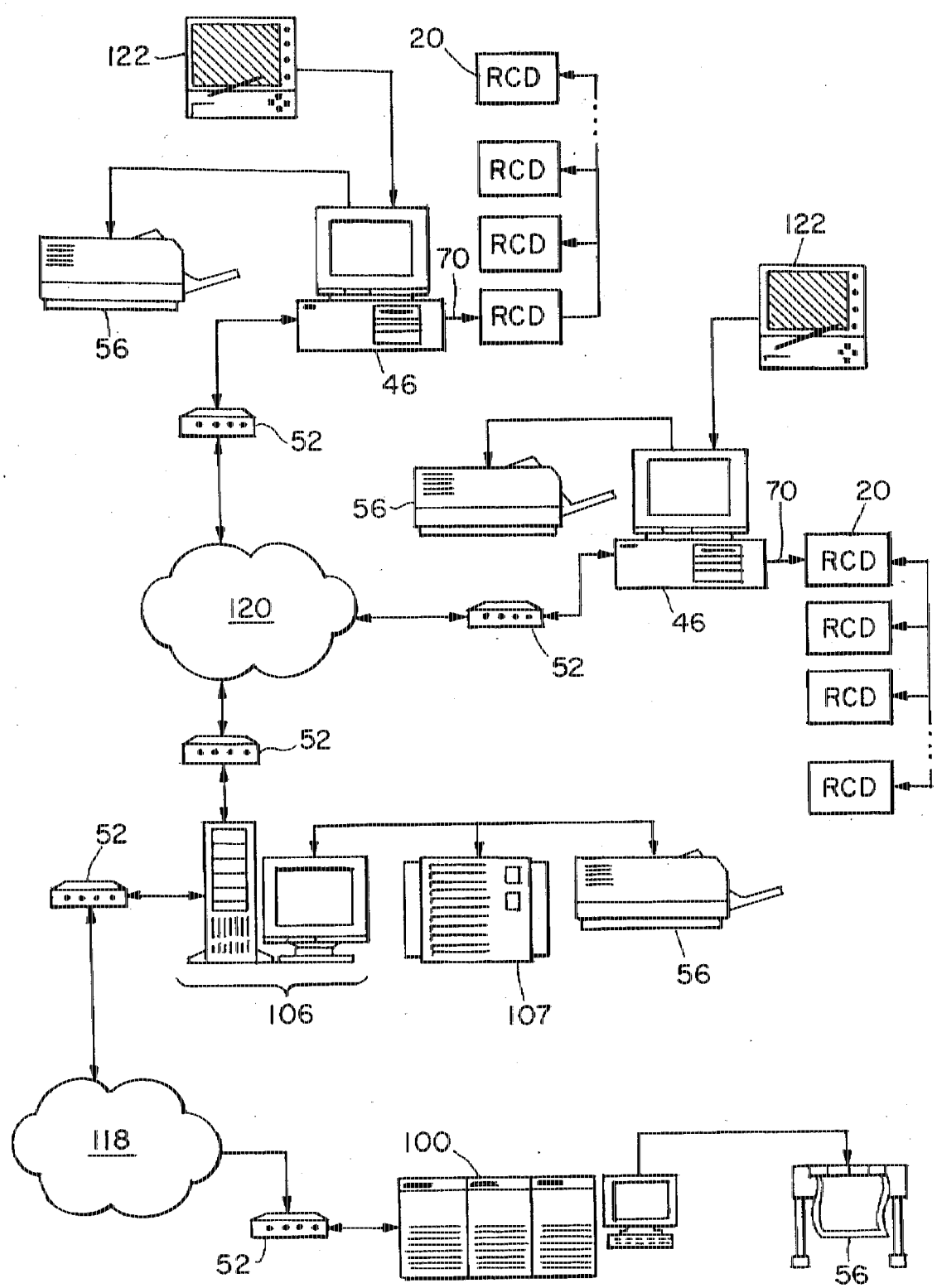
FIG. 4 is a block diagram of an automated drug dispensing system having daisy-chained remote control dispenser cabinets in accordance with the present invention.

FIG. 4 is a block diagram of a remote control dispensing configuration having daisy-chained remote drug dispensing units 20. A computer 100 at distribution headquarters is connected through a modem 52 to a bidirectional communication link 118. A computer 106, including disk storage 107 and a printer 56, at the municipal service center 106 communicates with headquarters 100 and with a plurality of remote control dispenser workstations 46 via modems 52. The RCD workstations 46 include a printer 56 and may include personal data assistants 122. The workstation 46 is connected via a controller interface 70 to remote control dispenser cabinets 20. The cabinets 20 can be daisy-chained as shown, or may each be individually connected to the workstation 46. The computer 100 can also be linked by modem to all or selected remote dispensers so that each dispenser can be remotely controlled.

Figure 5:
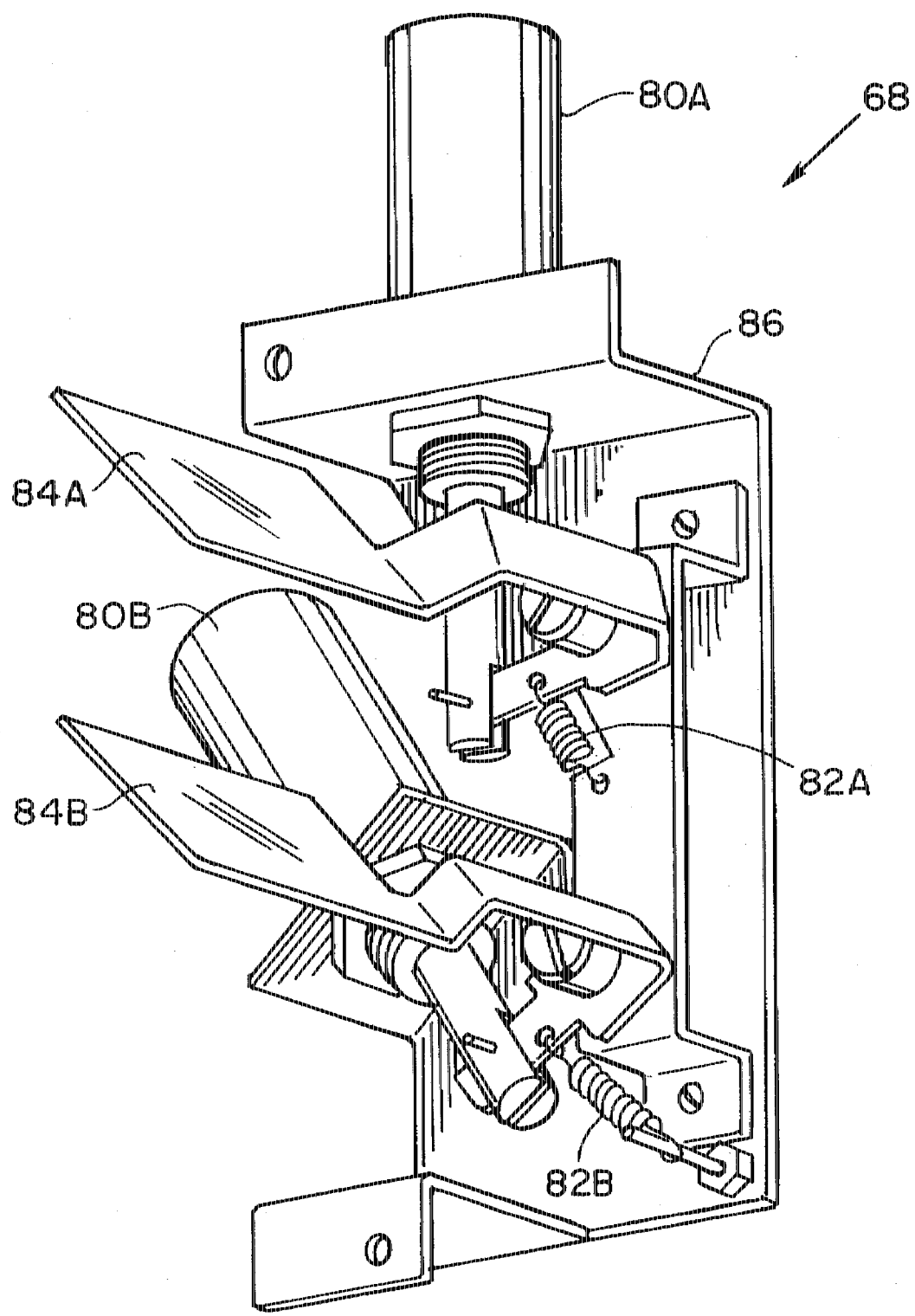
FIG. 5 is a perspective view of a dual-valve dispenser in accordance with the present invention.

FIG. 5 is a perspective view of a dual-valve dispenser 68. As shown in FIGS. 1 and 3, each column 34 includes a dispenser unit 68. The dispenser unit 68 is located at the bottom of each column for dispensing a single bottle 32 when commanded by the user. A preferred dispenser 68 includes an upper solenoid 80A and a lower solenoid 80B. Each solenoid 80A, 80B engages a corresponding dispenser valve 84A, 84B. The dispenser valves 84A, 84B are biased in a closed position by return springs 82A, 82B. All dispenser components are mounted to a housing 86.

Figure 6A:
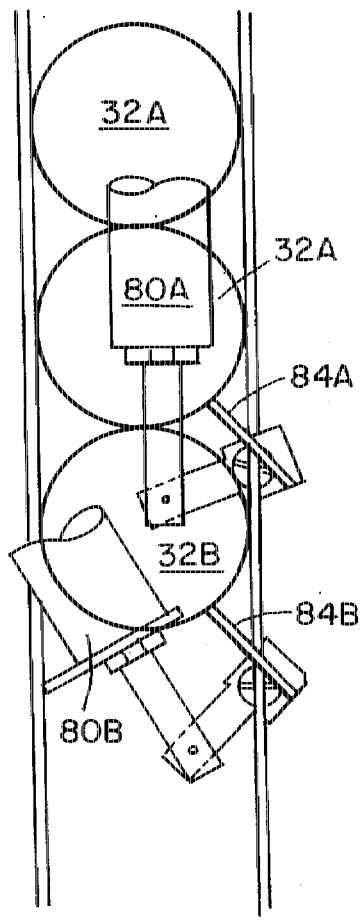
FIGS. 6A–6C are sequential illustrations of the operation of the dual-valve dispenser.
Figure 6B:
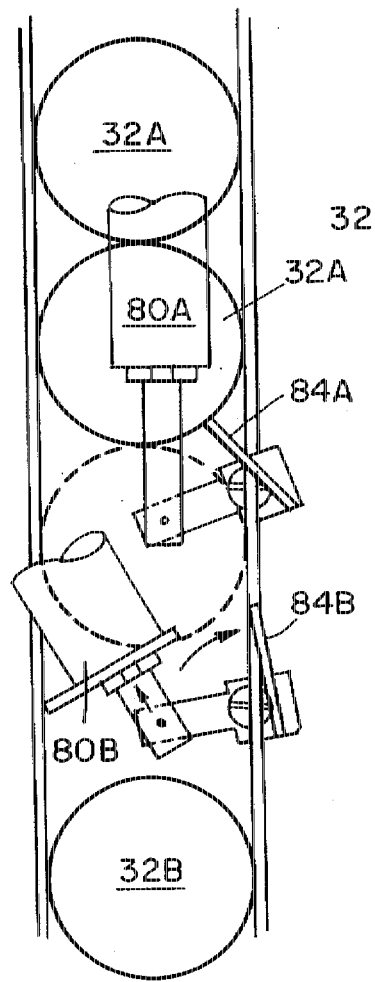
Figure 6C:
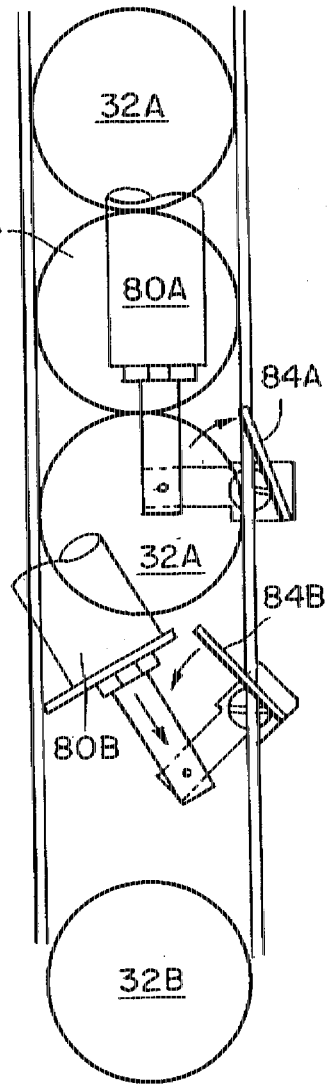

FIGS. 6A–6C illustrate operation of the dispenser valve during a dispensing sequence. In FIG. 6A, a gravity-fed column of bottles 32 is held in place by a bottle rack 24. A lower bottle 32B is retained by lower solenoid 80B and lower valve 84B and held in place between the valve 84B and the wall of the rack 24. The remaining bottles in the column 32A are retained by the upper solenoid 80A and upper valve 84A.

In FIG. 6B, the lower solenoid 80B retracts, preventing the lower valve 84B from interfering with the lower bottle 32B. This allows the lower bottle 32B to be released and dispensed. The upper bottles 32A continue to be held in position by upper valve 84A.

In FIG. 6C, the lower solenoid 80B is reactivated and lower valve 84B again interferes with the rack 24. The upper solenoid 80A is then retracted, disengaging the valve 84A from the upper bottles 32A. This allows the column 32A to fall and the lowest bottle engages the lower valve 84B. The upper solenoid 80A next closes the upper valve 84A, causing it to engage the next bottle 32A in the column. In this manner, a single bottle 32B is dispensed, the remaining bottles 32A all descend one position, and the dispenser 68 is again ready to dispense as shown in FIG. 6A.

Figure 7A:
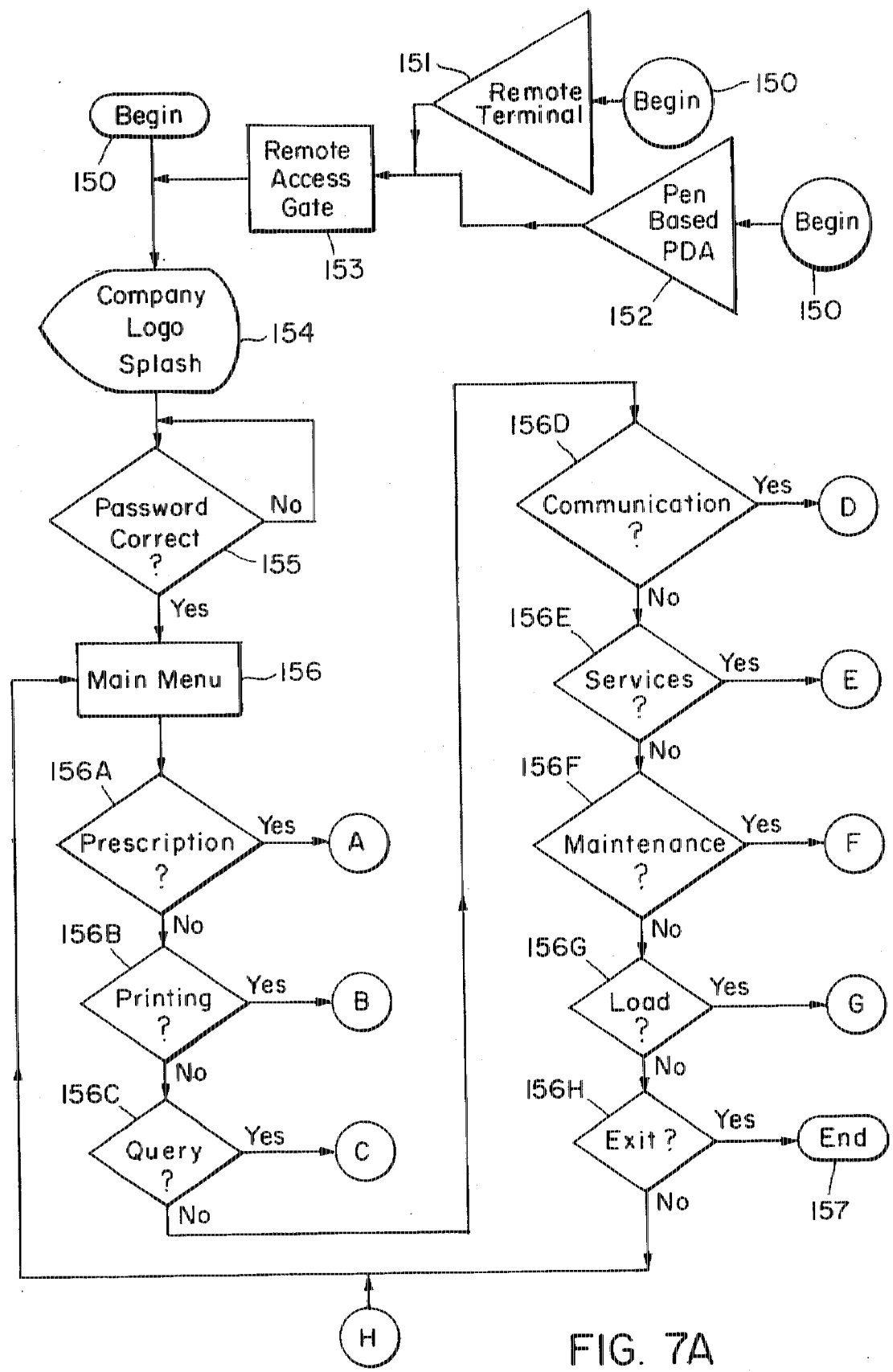
FIG. 7A is a flow diagram of the main menu software.
Figure 7B:
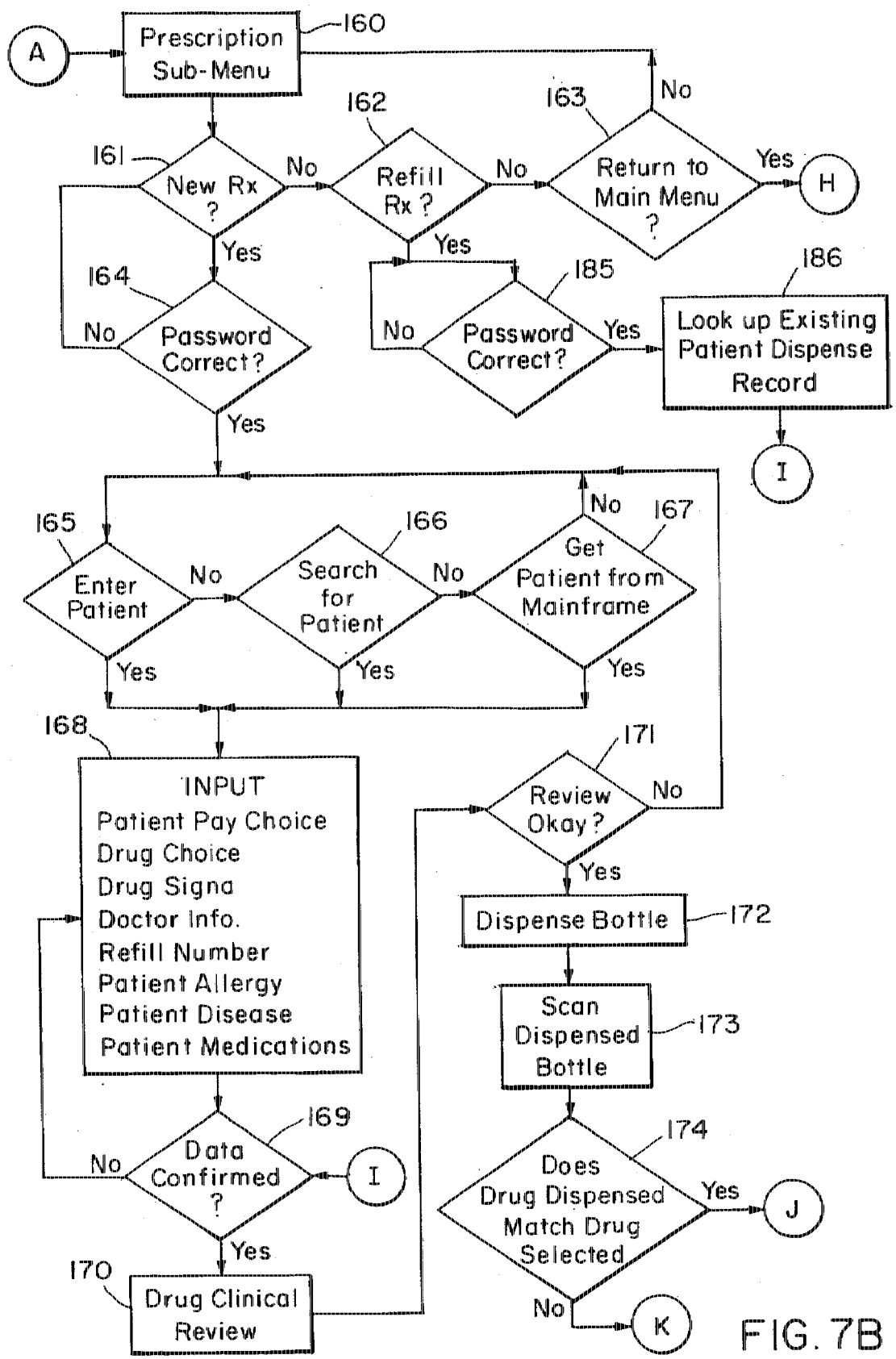
FIG. 7B and 7C are flow diagrams of the prescription menu software.
Figure 7C:
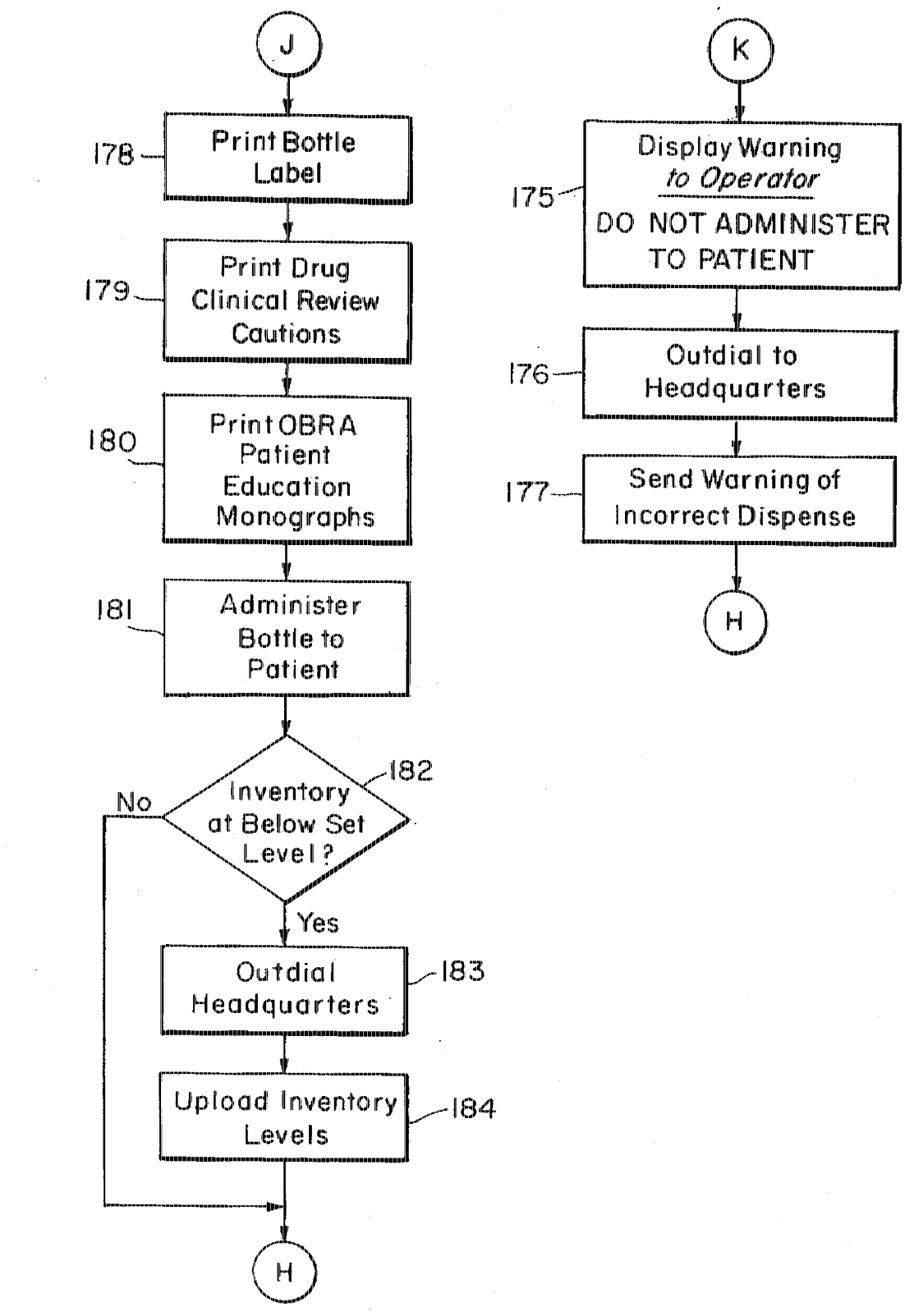

FIGS. 7A, 7B, and 7C are flow diagrams of the computer 46 software. The software is preferably in a user-friendly windows format. In a standard format, the software is accessed on the host computer. Alternatively, the software is accessible by a remote terminal 151 or a pen-based personal data assistant 152 through a remote access gate 153. A splash screen 154 containing the company name, for example is output on the screen and the user is queued for a password 155. If the password is entered correctly, a main menu 156 is generated requesting the user to: access a prescription 156A; print a report or label 156B; investigate the database 156C; communicate with a remote location 156D; service the database 156E; maintain the cabinet 156F; load additional software 156G; and exit 156H. If exit 156H is selected, the program ends 157.

FIG. 7B is a flow diagram of the prescription submenu 160. The computer queues the user as to whether he would like to enter a new prescription 161, refill an existing prescription 162, or return to the main menu 163. If the user selects the new prescription 161 option, he is queued for a password 164. The user is next asked to enter the patient name 165. If the name is not known, then a search program 166 can search for the patient name or download the patient name from a mainframe 167. When the patient name is known, the user enters various prescription information and confirms that the data entered is correct 169. Next, the software runs a clinical review 170 and determines whether the prescription is proper 171.

If the prescription is proper, a bottle is dispensed 172 and the bar code of the dispensed bottle is scanned 173. If the bar code does not match that which was expected 174, then a warning is displayed 175, see FIG. 7C a communication link is set up with headquarters 176 and headquarters is warned 177 of the incorrect dispensing. If the proper medication was dispensed 174, then the computer prints a bottle label 178, generates a clinical review report 179 and conducts OBRA patient education monographs 180. The bottle is then administered to the patient 181 and the computer checks inventory 182 and if inventory is low, the computer communicates with headquarters 183 and orders new inventory 184. The computer then returns to the main menu 156.

If the user selected the "refill prescription" option 162 at the prescription submenu 160, then the password is checked 185 and the current patient record is displayed 186. The practitioner confirms the data 169 and dispensing takes place in the manner described above.

Figure 2:
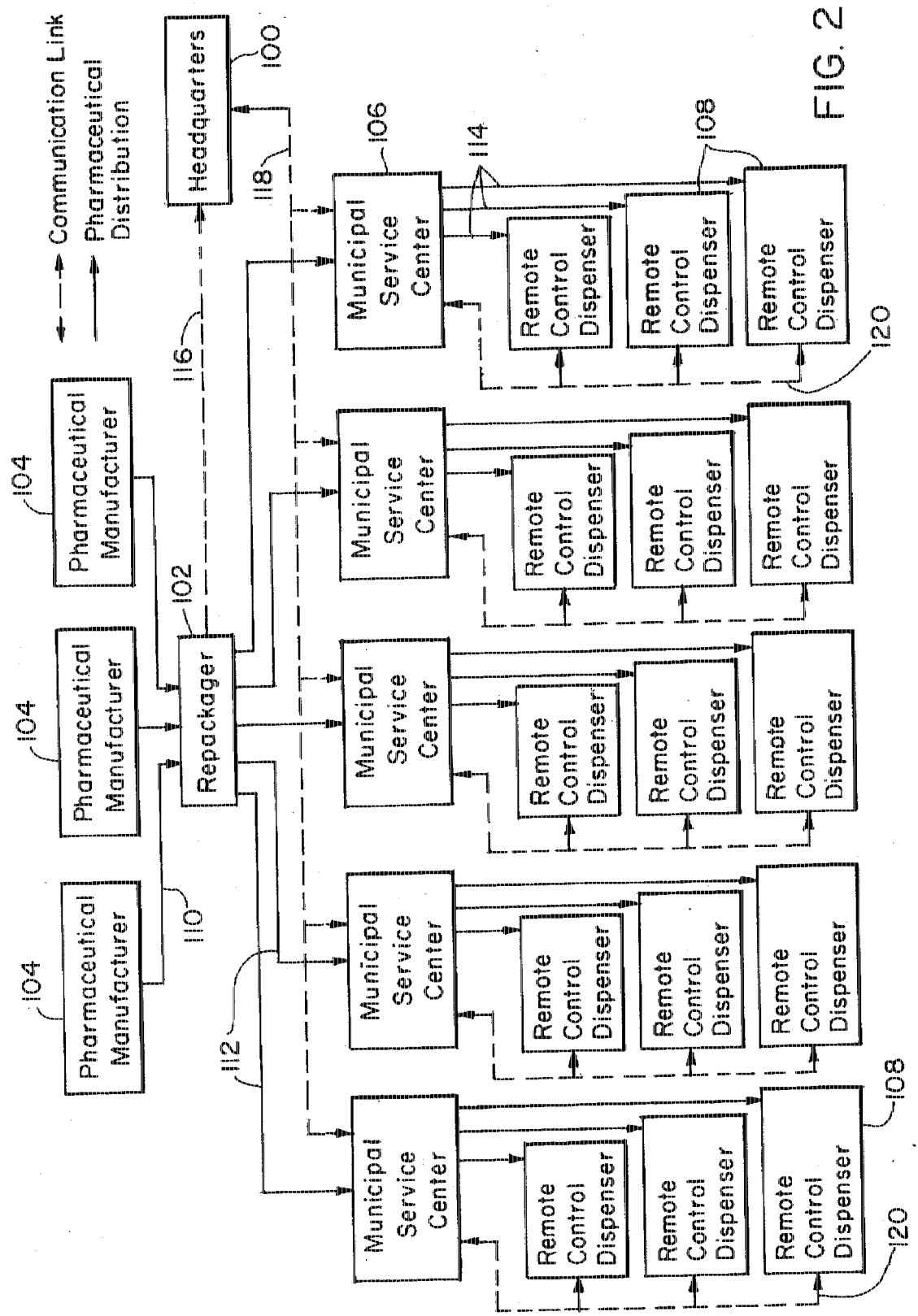
FIG. 2 is a block diagram of an automated system for pharmaceutical distribution and inventory management in accordance with the present invention.

FIG. 2 is a block diagram of an automated drug distribution system for maintaining the inventory of the RCD sites 108 in accordance with the present invention. The various RCD sites 108 are stocked with prepackaged pharmaceuticals obtained on a just-in-time (JIT) inventory basis from an FDA-approved drug repackager 102. The repackager 102 obtains unit-dose pharmaceuticals from various manufacturers 104, and repackages the unit-doses into a package containing multiple, prescription-sized doses. The packages must be suitable for use in the remote control dispenser units 108. The drugs are then distributed 112 to municipal service centers 106 which operate as regional distribution facilities in major urban areas. In turn, each municipal service center 106 redistributes 114 the packaged pharmaceuticals to each remote control dispenser 108 in its region.

The entire system is linked by a communication network 116, 118, 120. The inventory status of each remote control dispenser 120 is communicated to the corresponding municipal service center through a standard telephone link 120. Restocking requests and other inventory information are communicated 118 from the municipal service center 106 to headquarters 100 or any desired combination thereof. Headquarters 100 communicates 116 inventory requirements to the repackager 102. In response, the repackager 102 fills the order and ships the stock to the appropriate municipal service center 106. In this manner, headquarters 100 maintains an automated and continually-updated inventory of all remote control dispensers 108 on a JIT basis.

The system is further capable of monitoring patient records and billings and can format electronic third party billings for processing by the health care provider. With expanded software, patient records can be accessed on an integrated basis allowing for monitoring of drug side-effects and compliance.

In a preferred distribution system, a computer at the distributor headquarters 100 sends a restocking request via communication link 116 to the FDA-approved repackager 102. The repackager 102 fills the order and sends it by overnight air courier to the designated municipal service center 106. At the municipal service center, the drugs are distributed to drivers for specific remote control dispensers 108 in the local community. A driver delivers the drugs and restocks the remote control dispenser 108. As drugs are dispensed from the remote control dispenser 108, the inventory, sales, and restocking requirements are updated and transmitted via telephone link 120 to the computer at the municipal service center 106. The municipal service center computer is linked 118 to a similar computer at the distributor headquarters 100, completing the communication loop.

Pharmaceuticals are preferably bar-coded at the repackager 102. The pharmaceuticals are tracked using bar code information through each step of the process to the point of sale at the customer. In this way, all transactions are recorded and communicated in real-time to headquarters 100. This integrates accounting, accounts receivable, and inventory management systems, which allows the distributor headquarters to operate with minimal staffing. Each step of the process is self-contained and modular allowing rapid and flexible geographic expansion.

Each remote control dispenser is preferably placed on an inventory replenishment schedule. The number of weekly supply visits is a function of the rate of inventory usage. A computer record is maintained of prescriptions dispensed and product remaining. If there is a sudden increase in inventory activity, for example if a particular variety of medication is running low, an emergency call is initiated by the remote control dispenser 108 to the municipal service center 106 indicating the need for rapid inventory replenishment. The inventory preferably consists of the most frequently prescribed products used by physicians utilizing the unit. The variety can be adjusted at any time and will vary from location to location.

Figure 8:
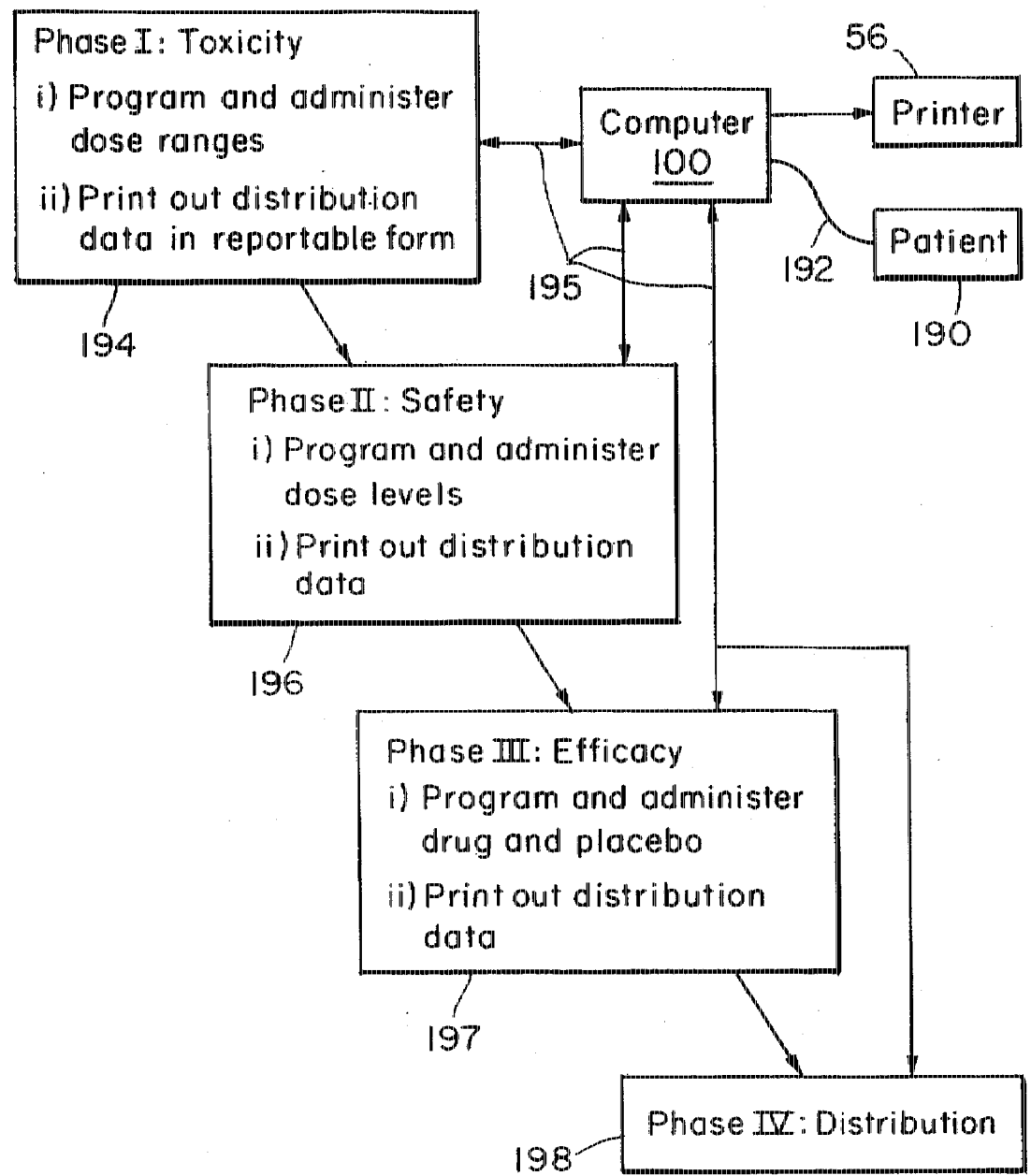
FIG. 8 is a schematic diagram illustrating the administration of a clinical trial in accordance with the invention.

A software module can be added to optimize use of the drug dispensing system for the administration of a clinical trial. As shown schematically in FIG. 8, clinical trials under current FDA regulations can be conducted in three phases; Phase I at 194 is to access toxicity; Phase II at 196 is to assess safety; Phase III at 197 is to assess efficacy, and possible Phase IV studies 198 for limited distribution. It is highly desirable to automate these procedures as the prompt and accurate evaluation of new treatments for safety and efficacy can lead to expedited regulatory review and approval.

The software is formatted to provide for administration of these three phases including the administration of the drug and a placebo in a so-called "double blind" procedure and to print out reports suitable for submission to the regulatory authority which include detailed data on distribution and dose. The computer records which packages contain placebos and which patients receive them. The computer 100 can record and execute various functions 195 in connection with these studies including printing of reports at printer 56, or communications along telephone line 192 for void activated or voice prompted follow up with the patient 190. These can include contacting the physician to report side effects or other information. A monogram on drug compliance is provided to each patient including drug interaction, side effects or dietary instructions.

Figure 9:
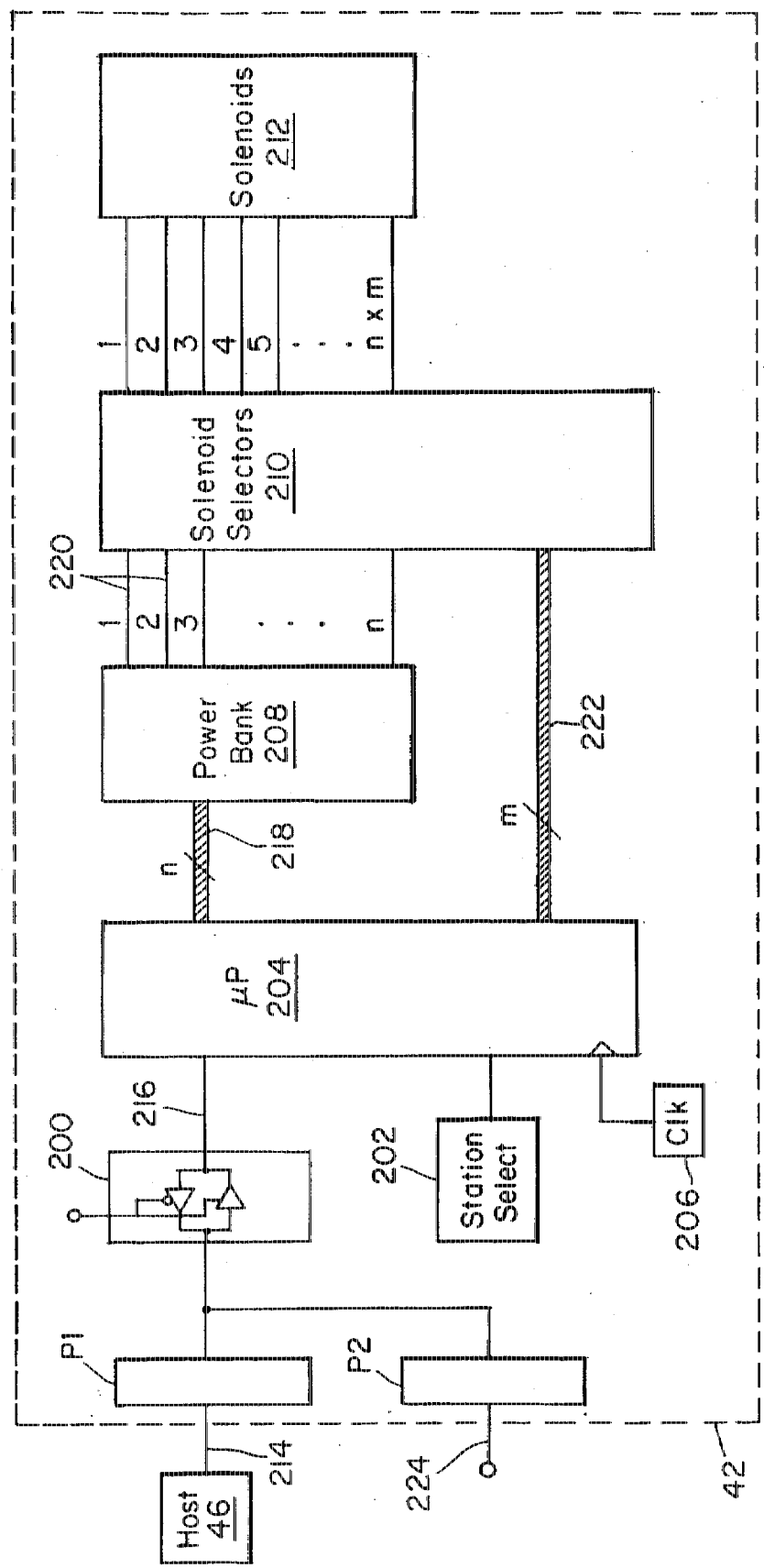
FIG. 9 is a schematic diagram of a circuit board using a controller for a drug dispensing system in accordance with the present invention.

FIG. 9 is a schematic block diagram of an RCD controller in accordance with the present invention. The host computer 46 is coupled to the RCD controller 42 via a standard serial interface, for example, an RS-232 interface. A port P1 receives the serial signal 214 and distributes it to a bidirectional tristate buffer 200. The buffered signal 216 enters a microprocessor 204 where it is decoded.

The microprocessor 204 decodes the serial signal 216 and activates an individual power blank line 218 and an individual solenoid line 222. The solenoids 212 are partitioned into n power banks 208, one power bank for each rack 24 in the cabinet. Each power bank 208 is activated by a data bus 218 output from the microprocessor 204. The power bank lines 220 are distributed to an array of solenoid selectors 210. The solenoid selectors combine the power bank signals 220 and solenoid signals 222 into an addressable array. If a power bank signal 220 is enabled, then power to the corresponding rack is activated. The solenoid signal 222 enables a particular solenoid 212 in the activated rack for dispensing. The solenoid signal bus 222 is m bits wide for selecting one of the m solenoids in the rack 24.

As stated above, the RCD cabinets can be daisy-chained so that a plurality of cabinets 20 are controlled by the same host computer 46. A second port P2 on the controller board 42 passes the serial signal 214 to the next board in the chain 224. A station-select switch 202 provides additional decoding so the controller 42 has knowledge of its address in the chain.

Figure 10:
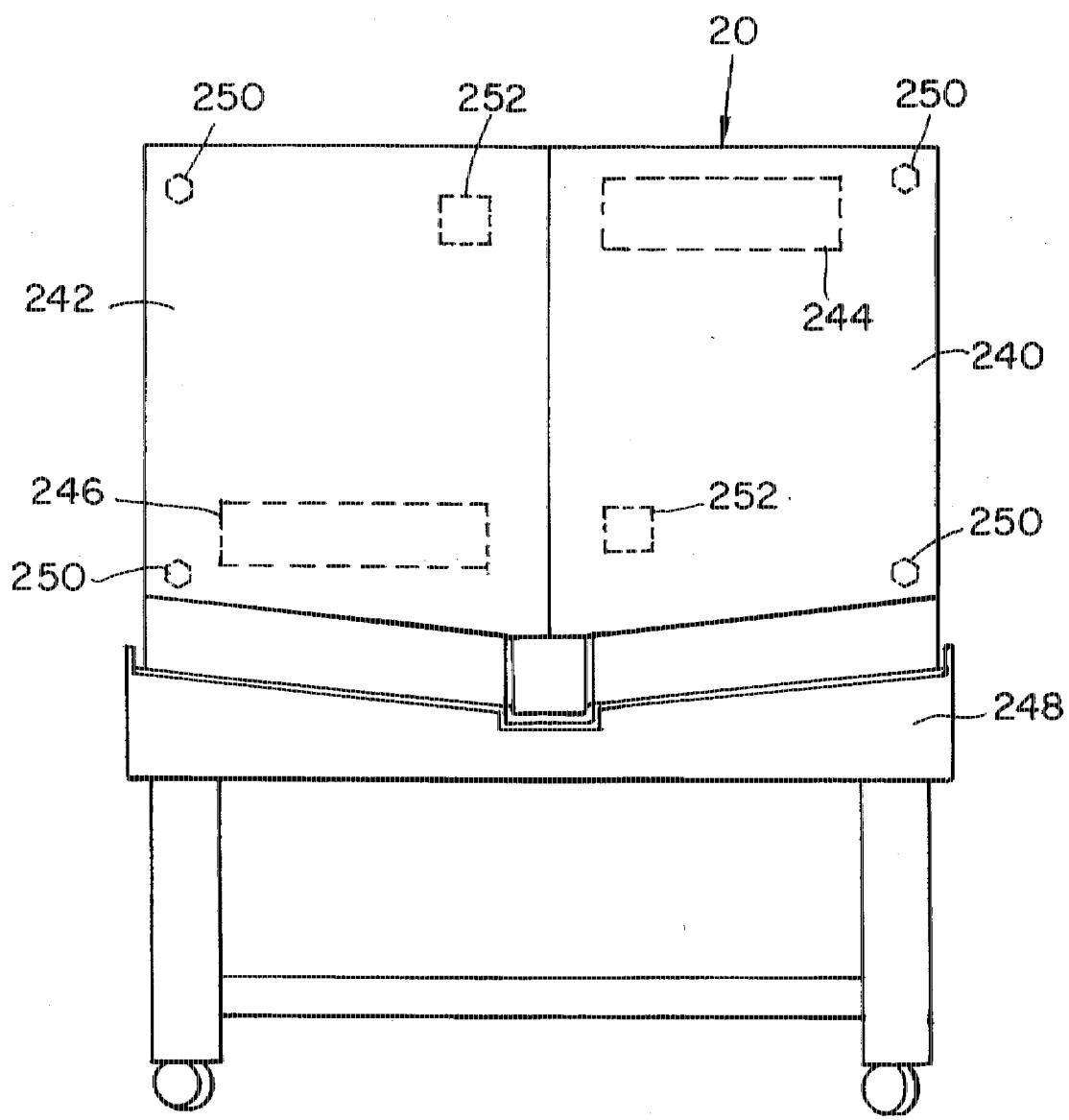
FIG. 10 is front view of a dispensing system on a rollable cart in accordance with the invention.

Another preferred embodiment of the invention is illustrated in connection with FIG. 10 where a dispensing cabinet 20 is positioned on a cart 248 having wheels and operable as a stand alone unit. The cart 248 can be used to support the unit relative to a wall surface in conjunction with bolts 250 or other suitable housing support mechanism. The housing support elements 250 can be used to support the cabinets 20 relative to the supporting surface without any other means for support.

Each cabinet 20 can also be insulated and provided with a cooling system 244 and/or a heating system 246. As illustrated, the cooling system 244 can be contained within the housing 20 on the frame of door panel 240. The heating systems can be used in the same panel 240 or in the adjoining panel 242. This system provides for the heating and/or cooling of selected drugs that require temperature regulation for storage. Many antibiotics, for example, must be maintained at a temperature of between 40°–50° F. to remain viable. One or more temperature sensors 252 can be positioned in the housing to monitor temperatures which can be regulated by controller and be recorded in computer 100 memory.

While this invention has been particularly shown and described with references to preferred embodiments thereof, it will be understood by those skilled in the art that various changes in form and details may be made therein without departing from the spirit and scope of the invention as defined by the appended claims.

We claim:

1. A system for automated dispensing of a packaged pharmaceutical comprising:
   an electronic controller for generating a dispense signal in response to a request signal;
   a housing having a plurality of bins, each bin storing a coded plurality of bottled pharmaceuticals, each of said bins having a bottle dispenser actuated by said electronic controller and that dispenses a bottled pharmaceutical therefrom in response to said dispense signal;
   a computer electrically connected to the electronic controller, the computer having a memory; and
   a code reader electrically connected to said computer for reading the code of a dispensed bottle, such that the computer records in the memory that the bottle has been dispensed.

2. The system of claim 1 wherein said bins comprise columns, said bottles being gravity-fed in the columns.

3. The system of claim 1 wherein said code reader comprises a bar code reader and the pharmaceutical bottles are coded with bar codes.

4. The system of claim 1 wherein said controller comprises a computer.

5. The system of claim 1 further comprising sensors coupled to said controller for monitoring inventory of said bottles.

6. The system of claim 1 further comprising a label printer for printing a prescription label for attaching to said dispensed pharmaceutical bottle.

7. The system of claim 6 wherein the printed prescription label includes a printed picture of the pharmaceutical contained in the dispensed bottle.

8. The system of claim 1 further comprising a document printer for printing instructions specific to said dispensed pharmaceutical bottle.

9. The system of claim 1 wherein said housing is adapted for mounting on a wall and the code reader for reading the code of a dispensed bottle is carried by the housing.

10. The system of claim 1 further comprising a ramp for delivering said dispensed pharmaceutical to a dispensing area and the code reader is adjacent the dispensing area for reading the code of a dispensed bottle.

11. The system of claim 10 wherein said ramp is sloped such that gravity delivers said dispensed pharmaceutical to said dispensing area.

12. The system of claim 1 wherein the code reader comprises a code reader mounted to the housing such that the code reader reads a dispensed bottle.

13. The system of claim 1 wherein the code reader comprises a hand held code reader.

14. A system for automated dispensing of a packaged pharmaceutical comprising:
   a controller for generating a dispense signal in response to a request signal;
   a housing having a plurality of bins, each bin storing a coded plurality of packaged pharmaceuticals, each of said bins having a dispenser coupled to said controller for dispensing said packaged pharmaceutical therefrom in response to said dispense signal;
   a plurality of valves actuated by a corresponding plurality of solenoids, said solenoids being sequentially activated such that a single package is dispensed from a column per request; and
   a code reader coupled to said controller for reading the code of a dispensed package, such that the controller records that the package has been dispensed.

15. A method for automated dispensing of a packaged pharmaceutical comprising:
   storing an encoded plurality of packaged pharmaceuticals in a bin, a plurality of the bins being contained in a housing;
   receiving request signals at a controller;
   generating dispense signals in response to the received request signals;
   dispensing a packaged pharmaceutical from a bin in response to the dispense signal;
   reading the code of a dispensed package with a code reader; and
   verifying that the requested package was dispensed by comparison of the code read by the code reader to a reference code.

16. The method of claim 15 further comprising the step of printing a prescription label at a label printer for attaching to the dispensed pharmaceutical package.

17. The method of claim 16 further comprising the step of printing a picture of the pharmaceutical pill on the label.

18. The method of claim 15 further comprising the step of delivering said dispensed pharmaceutical to a dispensing area with a ramp and the reading the code of a dispensed package with the code reader occurring at the dispensing area.

19. The method of claim 15 further comprising providing a plurality of multi-dose pills in each package.

20. The method of claim 15 further comprising providing each packaged pharmaceutical in a plastic bottle.

21. The method of claim 15 further comprising providing a fluid within each package.

22. The method of claim 14 further comprising providing a computer connected to the controller with a modem.

23. A method for automated dispensing of a packaged pharmaceutical comprising:
   storing an encoded plurality of packaged pharmaceuticals in a bin, a plurality of the bins being contained in a housing;
   receiving request signals at a controller;
   generating dispense signals in response to the received request signals;
   dispensing a packaged pharmaceutical with a dual valve dispenser from a bin in response to the dispense signal;
   reading the code of a dispensed package with a code reader; and
   verifying that the requested package was dispensed.

24. A method for automated dispensing of a packaged pharmaceutical comprising:
   storing an encoded plurality of packaged pharmaceuticals in a bin, a plurality of the bins being contained in a housing;
   receiving request signals at a controller;
   generating dispense signals in response to the received request signals;
   dispensing a packaged pharmaceutical with a gas ejector from a bin in response to the dispense signal;
   reading the code of a dispensed package with a code reader; and
   verifying that the requested package was dispensed.

25. A method for automated dispensing of a packaged pharmaceutical comprising:

storing an encoded plurality of packaged pharmaceuticals in a bin, a plurality of the bins being contained in a housing;

receiving request signals at a controller;

generating dispense signals in response to the received request signals;

dispensing a packaged pharmaceutical from a bin in response to the dispense signal;

reading the code of a dispensed package with a code reader;

verifying that the requested package was dispensed; and conducting a clinical drug trial.

26. The method of claim 25 further comprising loading the housing with a first plurality of packages of a selected drug and a second plurality of packages of a selected placebo.

27. A method for automated dispensing of a packaged pharmaceutical and of loading the packaged pharmaceutical from a housing comprising:

storing an encoded plurality of packaged pharmaceuticals in a bin, a plurality of the bins being contained in the housing;

receiving request signals at a controller;

generating dispense signals in response to the received request signals;

dispensing a packaged pharmaceutical from a bin in response to the dispense signal;

reading the code of a dispensed package with a code reader;

verifying that the requested package was dispensed;

monitoring an amount of packages within the housing;

generating a reload signal;

opening the housing;

scanning packages with a bar code reader as the packages are loaded into the housing; and recording data in a memory regarding the loaded packages.

28. The method of claim 27 further comprising scanning the packages with a hand-held bar code reader.

29. The method of claim 27 further comprising monitoring the packages in a bin with a sensor.

30. A method for automated dispensing of a packaged pharmaceutical comprising:

storing an encoded plurality of packaged pharmaceuticals in a bin, a plurality of the bins being contained in a housing;

receiving request signals at a controller;

generating dispense signals in response to the received request signals;

dispensing a packaged pharmaceutical from a bin in response to the dispense signal, the packaged pharmaceutical having been separated from other packaged pharmaceuticals in the bin, by dropping the packaged pharmaceutical from the bin to a dispensing area on the housing;

subsequently reading the code of a dispensed package with a code reader; and verifying that the requested package was dispensed.

31. The method of claim 30 further comprising the step of printing a prescription label at a label printer for attaching to the dispensed pharmaceutical package.

32. The method of claim 30 further comprising the step of delivering said dispensed pharmaceutical to a dispensing area with a ramp and the reading the code of a dispensed package with the code reader occurring at the dispensing area.

* * * * *